United States Patent
Lucio

(10) Patent No.: US 10,617,839 B2
(45) Date of Patent: Apr. 14, 2020

(54) PORTABLE OXYGEN CONCENTRATOR FOR RECREATION AND HIGH ALTITUDE SPORTS

(71) Applicant: Albert A. Lucio, Haines City, FL (US)

(72) Inventor: Albert A. Lucio, Haines City, FL (US)

(*) Notice: Subject to any disclaimer, the term of this patent is extended or adjusted under 35 U.S.C. 154(b) by 273 days.

(21) Appl. No.: 15/866,914

(22) Filed: Jan. 10, 2018

(65) Prior Publication Data

US 2019/0184128 A1 Jun. 20, 2019

Related U.S. Application Data

(60) Provisional application No. 62/598,497, filed on Dec. 14, 2017.

(51) Int. Cl.
*A61M 16/10* (2006.01)
*C01B 13/02* (2006.01)
(Continued)

(52) U.S. Cl.
CPC ........ *A61M 16/101* (2014.02); *A61M 16/107* (2014.02); *B01D 53/047* (2013.01);
(Continued)

(58) Field of Classification Search
CPC .............. A61M 16/101; A61M 16/105; A61M 16/106; A61M 16/107; A61M 2202/0208; A61M 16/0677; A61M 16/0666; A61M 16/0672; A61M 2205/8206; A61M 16/0003; A61M 16/10; A61M 2202/0007; A61M 2205/75; A61M 2209/088; A61M 16/00; A61M 16/0063; A61M 16/0072; A61M 16/06; A61M 16/0683; A61M 16/0833; A61M 16/0875; A61M 16/1005; A61M 16/1055; A61M 16/12; A61M 16/20; A61M 16/202; A61M 16/204; A61M 16/206; A61M 16/208; A61M 2016/0021; A61M 2016/0033; A61M 2016/1025; A61M 2202/025; A61M 2202/03; A61M 2205/02; A61M 2205/18; A61M 2205/3327; A61M 2205/3334;
(Continued)

(56) References Cited

U.S. PATENT DOCUMENTS

| 6,065,473 A | 5/2000 | McCombs et al. |
| 6,241,704 B1 * | 6/2001 | Peterson ........... A61M 5/14228 |
| | | 604/65 |

(Continued)

OTHER PUBLICATIONS

Aero Mobile Oxygen (website), posted Feb. 11, 2017.*
(Continued)

*Primary Examiner* — Kendra D Carter
*Assistant Examiner* — Elliot S Ruddie
(74) *Attorney, Agent, or Firm* — Carlson, Gaskey & Olds, P.C.

(57) ABSTRACT

This disclosure relates to a portable oxygen concentrator system. The system includes a case containing a portable oxygen concentrator, a mask, and a button. The case is configured to be worn on a user's back. The mask is configured to deliver oxygen from the portable oxygen concentrator to the user. The button, when activated, is configured to cause the portable oxygen concentrator to deliver an increased flow of oxygen to the user for a period of time.

20 Claims, 5 Drawing Sheets

(51) Int. Cl.
*B01D 53/047* (2006.01)
*A61M 16/00* (2006.01)
*A61M 16/06* (2006.01)

(52) U.S. Cl.
CPC ......... *C01B 13/02* (2013.01); *A61M 16/0063* (2014.02); *A61M 16/022* (2017.08); *A61M 16/0683* (2013.01); *A61M 16/0688* (2014.02); *A61M 2016/1025* (2013.01); *A61M 2202/0208* (2013.01); *A61M 2202/0266* (2013.01); *A61M 2205/3334* (2013.01); *A61M 2205/502* (2013.01); *A61M 2205/8206* (2013.01); *A61M 2209/088* (2013.01); *A61M 2210/10* (2013.01); *A63B 2213/006* (2013.01); *B01D 2256/12* (2013.01); *B01D 2257/102* (2013.01); *B01D 2259/40007* (2013.01); *B01D 2259/4533* (2013.01); *B01D 2259/4541* (2013.01)

(58) Field of Classification Search
CPC .. A61M 2205/3569; A61M 2205/3584; A61M 2205/3592; A61M 2205/42; A61M 2205/502; A61M 2205/52; A61M 2205/581; A61M 2205/582; A61M 2205/80; A61M 2205/82; A61M 2205/8212; A61M 2205/8293; A61M 2230/04; A61M 2230/202; A61M 2230/205; A61M 2230/42; A61M 2230/432; A61M 2230/63; A63B 2213/00; A63B 2213/005; A63B 2213/006; B01D 2257/10; B01D 2257/102; B01D 2257/104; B01D 2259/45; B01D 2259/4533; B01D 2259/4541

USPC .................................................. 128/201.21
See application file for complete search history.

(56) References Cited

U.S. PATENT DOCUMENTS

| | | | |
|---|---|---|---|
| 7,121,276 | B2 | 10/2006 | Jagger et al. |
| 7,984,711 | B2 * | 7/2011 | Schipper .................. A45F 3/04 128/202.13 |
| 8,196,582 | B2 | 6/2012 | Ogilvie |
| 9,839,757 | B2 | 12/2017 | Galbraith |
| 2006/0174876 | A1 * | 8/2006 | Jagger .................. A61M 16/10 128/201.21 |
| 2007/0056500 | A1 * | 3/2007 | Beck ...................... A62B 33/00 116/210 |
| 2008/0223369 | A1 | 9/2008 | Warren |
| 2010/0263664 | A1 | 10/2010 | Radivojevic et al. |
| 2014/0007870 | A1 | 1/2014 | Franberg et al. |
| 2015/0196727 | A1 | 7/2015 | Ahmad |
| 2016/0175866 | A1 | 6/2016 | Kalalau |
| 2017/0148440 | A1 | 5/2017 | Coleman |
| 2017/0348501 | A1 | 12/2017 | Taylor et al. |

OTHER PUBLICATIONS

Litch JA, Bishop RA. Oxygen concentrators for the delivery of supplemental oxygen in remote high-altitude areas. Wilderness Environ Med. Sep. 2000;11(3):189-91.*

* cited by examiner

PORTABLE OXYGEN CONCENTRATOR FOR RECREATION AND HIGH ALTITUDE SPORTS

RELATED APPLICATIONS

This application claims the benefit of U.S. Provisional Application No. 62/598,497 filed Dec. 14, 2017, the entirety of which is herein incorporated by reference.

BACKGROUND

This disclosure relates to a portable oxygen concentrator for sporting and recreational use.

Portable oxygen concentrators (POCs) are commonly used in the medical field to supply supplemental oxygen to a patient. In their most common applications, POCs are used to treat a variety of conditions, such as heart failure, Chronic Obstructive Pulmonary Disease (COPD), or any weakened lung or heart state. Generally, POCs filter ambient air, leaving only oxygen, and supply that oxygen to the patient. POCs for medical treatment are regulated by the FDA and require a prescription from a physician. Known POCs either deliver a pulse dose or a continuous flow of oxygen to the patient. Pulse dose (sometimes called pulse flow) POCs provide oxygen only when the patient is inhaling, while continuous flow POCs provide a continuous stream of oxygen.

At times, supplemental oxygen is used for recreational purposes, such as to shorten recovery time for exhausted players at sports games. Supplemental oxygen may also be used at high altitudes to make breathing easier for skiing, or other sporting activities. There is a need for an apparatus designed for recreational sporting use.

SUMMARY

This disclosure relates to a portable oxygen concentrator (POC) system. A system according to an exemplary aspect of the present disclosure includes a case containing a portable oxygen concentrator, a mask, and a button. The case is configured to be worn on a user's back. The mask is configured to deliver oxygen from the portable oxygen concentrator to the user. The button, when activated, is configured to cause the portable oxygen concentrator to deliver an increased flow of oxygen to the user for a period of time.

According to another exemplary aspect of the present disclosure, a POC includes a filter configured to deliver an oxygen purity of less than about 86% in normal conditions.

According to another exemplary aspect of the present disclosure, a POC system includes a case containing a portable oxygen concentrator. The portable oxygen concentrator has a base pulse flow and a boost pulse flow, and can only be used at either the base pulse flow or the boost pulse flow settings. The base pulse flow is fixed between about 1 and about 3 liters per minute.

DETAILED DESCRIPTION

This disclosure relates to a portable oxygen concentrator (POC) which has particular benefits when used during sporting or recreational activities, such as high altitude skiing or biking, as examples.

Figure 1:
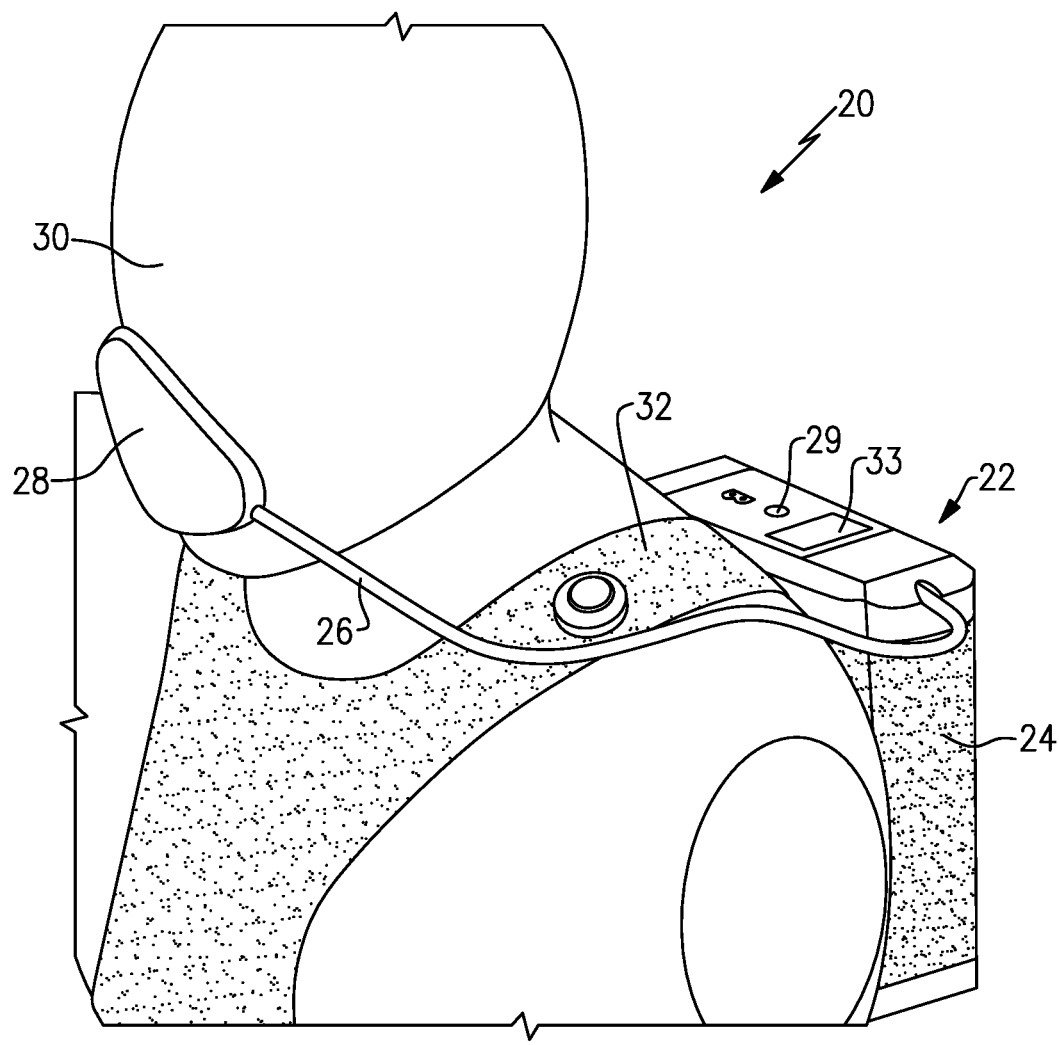
FIG. 1 illustrates an example POC system.

Referring to the drawings, FIG. 1 illustrates an example POC system 20. The system 20 includes a POC 22 in a case 24. The POC 22 delivers oxygen via a conduit 26 to a mask 28, which delivers the oxygen to a user 30. In the illustrated embodiment, the case 24 is a backpack with shoulder straps 32. This disclosure extends to other cases, however. Further, in the illustrated embodiment, the shoulder straps 32 are joined at a chest area of the user 30. In other embodiments, the shoulder straps 32 may be separate. Further, in this example, the POC 22 has a power button 29 and a display 33, which shows the current operating state of the POC 22, among other information. The display 33 may show the oxygen purity or pulse flow rate, for example.

Figure 2:
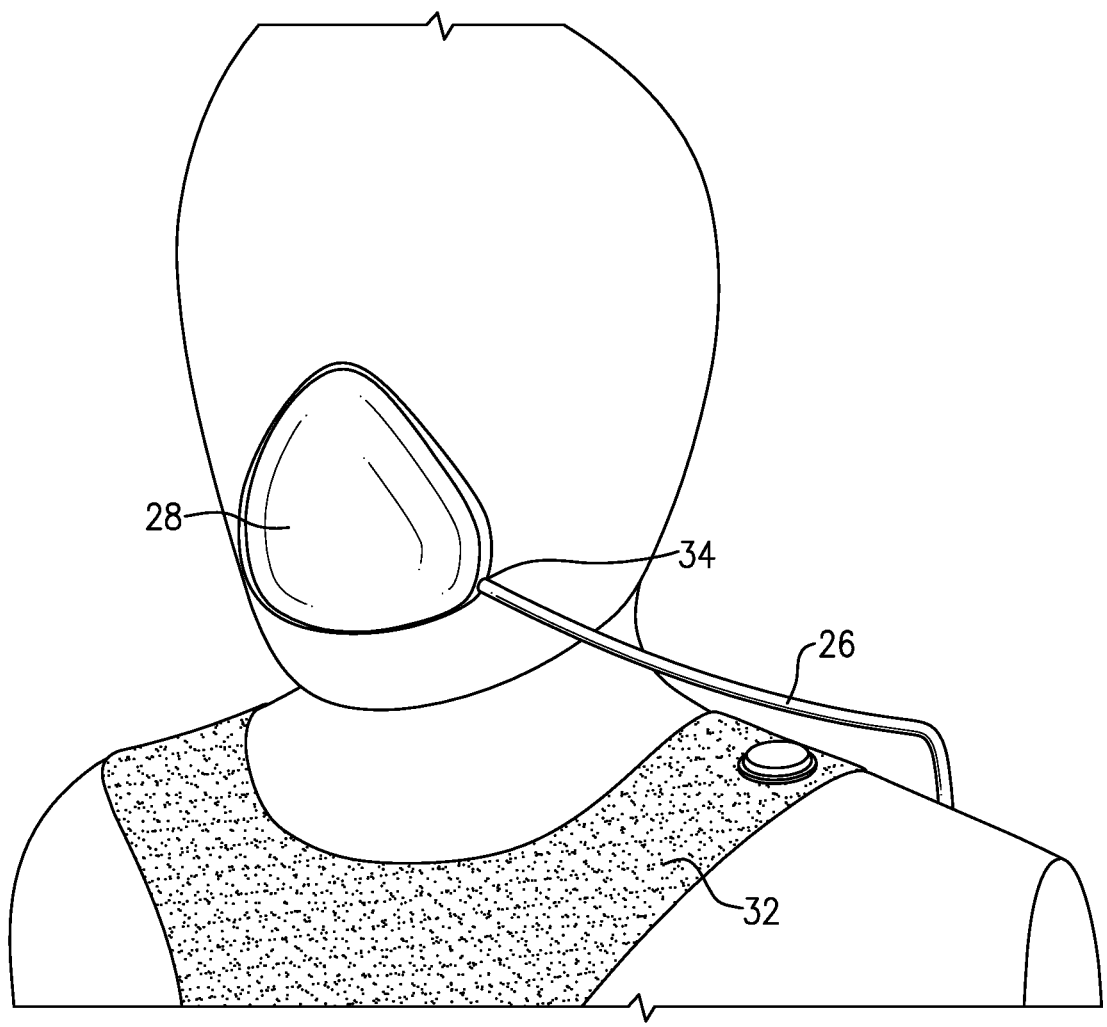
FIG. 2 illustrates the POC system of FIG. 1 in a front-perspective view.

FIG. 2 illustrates a front view of the POC system 20. The mask 28 is shaped to contour around a user's mouth and nose. This disclosure is not limited to any particular type of mask, however. The mask 28 includes an aperture 34 configured to couple to the conduit 26 for delivering oxygen flow. In some embodiments, the mask 28 is made entirely or partially of silicone, or other soft elastomer. The mask 28 may be provided in different sizes to accommodate different users 30. In one embodiment, the mask 28 may be secured to the user's face with a strap or with an adhesive.

Figure 3:
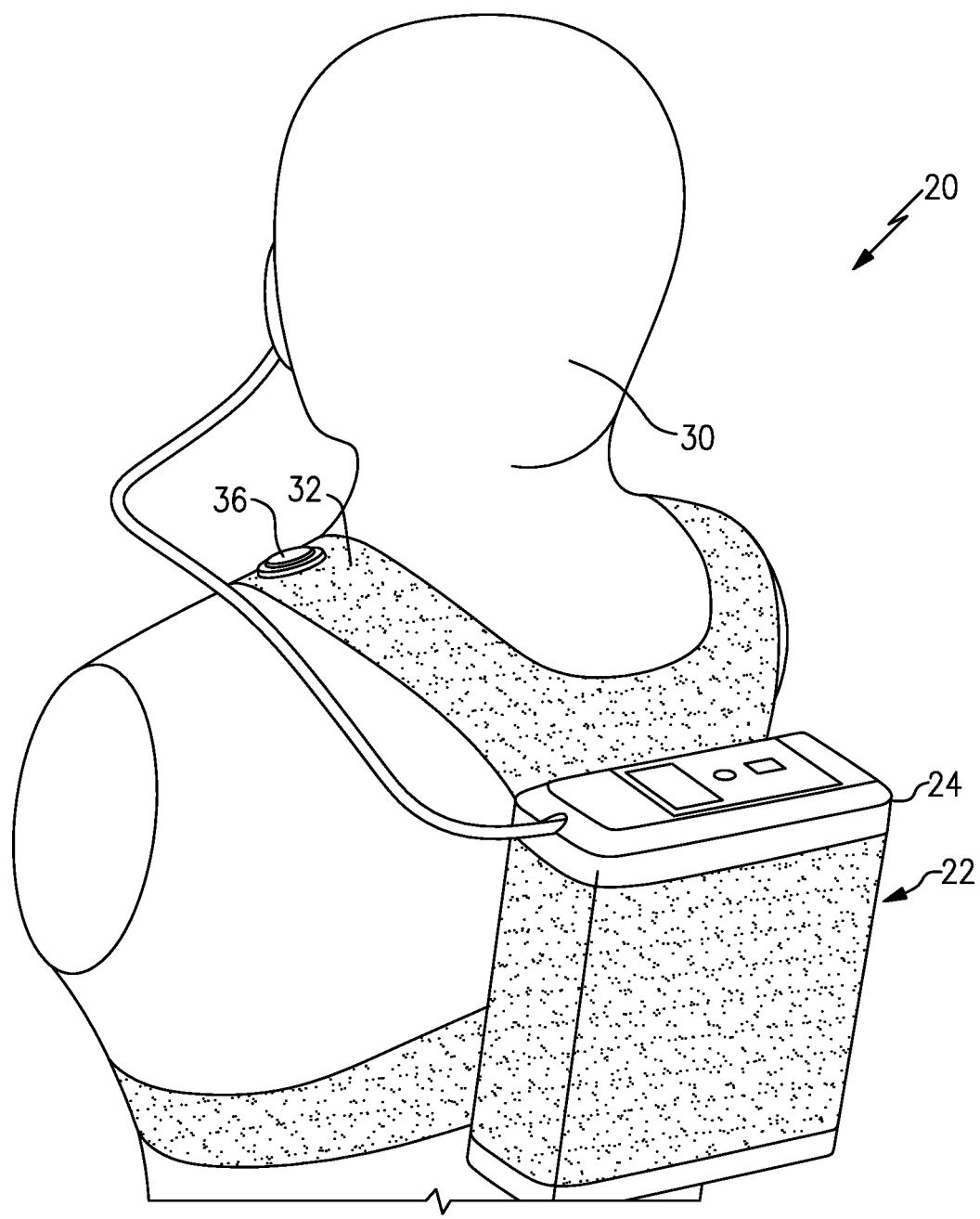
FIG. 3 illustrates the POC system of FIG. 1 in a back-perspective view.

FIG. 3 illustrates a perspective view of the POC system 20. In an embodiment, the POC 22 includes an air compressor, a filter, and a battery. In an embodiment, the filter is a molecular sieve which adsorbs nitrogen from the ambient air. The POC 22 may use pressure swing adsorption (PSA), vacuum swing adsorption (VSA), or pressure vacuum swing adsorption (PVSA) technology. The POC 22 may further include a storage chamber. The battery may be rechargeable. Each of these components fits within the case 24.

In one example, ambient air contains about 21% oxygen and about 79% nitrogen and other gases. The POC 22 compresses the ambient air and filters the nitrogen out of the air, leaving oxygen as the primary gas. The nitrogen is released back to the ambient environment. In a typical medical POC, the gas delivered to a patient is around 90-95% oxygen. The disclosed POC 22 delivers an oxygen purity of less than 90%. In a further embodiment, the POC 22 delivers an oxygen purity of less than 86%. In yet a further embodiment, the POC 22, delivers an oxygen purity of less than 80%. In an example embodiment, the POC 22 may deliver an oxygen purity of about 85%. The POC 22 delivers an oxygen purity lower than that required by the U.S. Food and Drug Administration for a POC used to treat medical conditions. Thus, the POC 22 is not a medical device, and does not require a prescription.

The POC 22 is a pulse delivery device in this example. That is, the POC 22 only provides oxygen when the patient is inhaling. Thus, there is a reduced load on the POC 22 compared to a continuous flow device. In an embodiment, the POC 22 is designed to deliver a base fixed pulse flow in the range of 1 to 3 liters per minute (LPM). In a further embodiment, the POC 22 may deliver a fixed base pulse flow of about 2 LPM. The POC may have a "boost" feature, which increases the pulse flow to a boost pulse flow for a finite period of time. The finite period of time may be predetermined and set by a manufacturer. Alternatively, the finite period of time can be set by a user. For example, when activated, the boost may increase the flow from about 2 LPM to about 5 LPM for 1 to 10 minutes. In a further example, the boost lasts for five minutes. In yet a further example, the boost pulse flow is about 5 LPM. The system 20 may include a button 36 to activate the boost feature. This boost feature may be used when the user 30 needs a higher oxygen intake, such as periods of increased exertion. For example, a cyclist may activate the boost feature when pedaling uphill, and after the fixed duration of time, the pulse flow returns to the base pulse flow. In some examples, the POC 22 only operates at the base pulse flow or the boost pulse flow, and is not otherwise adjustable.

The POC 22 only needs two buttons, in this example. Those buttons are the power button 29, which powers the device on and off, and the boost button 36, which is selectively activated to increase the flow rate for a duration of time. The POC 22 is set to deliver a pre-set fixed pulse flow when on with no ability to change the pulse flow, other than the boost feature. Thus, the POC 22 is much simpler than a medical POC, which may have multiple settings. Such medical POCs often include flow control buttons and indicators for breath detection or alerts, and sometimes include the ability to toggle between a continuous flow and a pulse flow.

Figure 4:
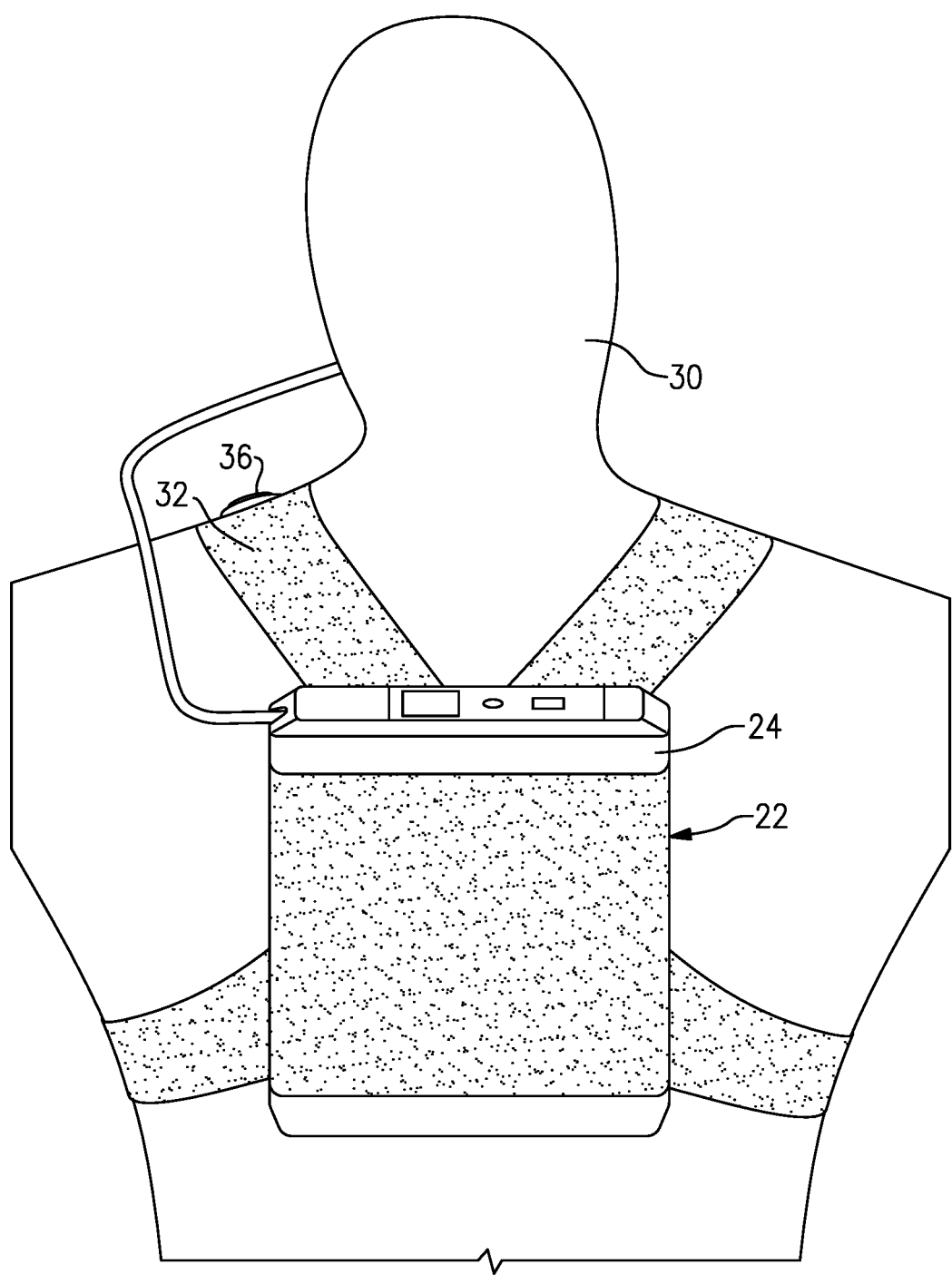
FIG. 4 illustrates the POC system of FIG. 1 in a back view.
Figure 5:
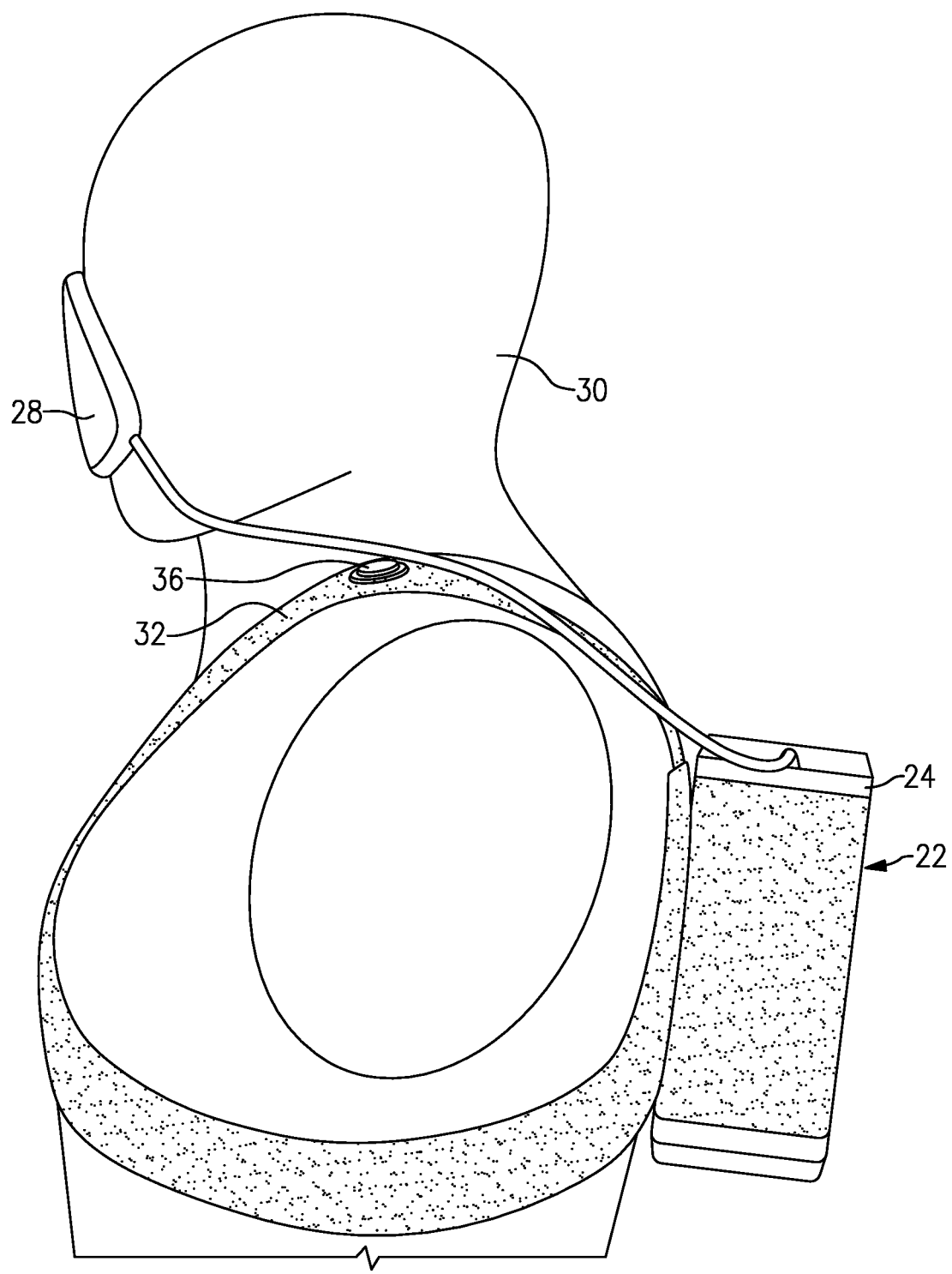
FIG. 5 illustrates the POC system of FIG. 1 in a side view.

FIGS. 4 and 5 show a back and side view of the system 20, respectively. In the illustrated embodiment, the button 36 is positioned on a shoulder strap 32, such that it is on a left shoulder of the user 30 when the user 30 wears the system 20. This button 36 may be used to activate the boost feature while the user 30 is wearing the system 20. The button 36 may be in other locations, and should be placed such that the user 30 may easily reach the button 36 while wearing the system 20. For example, in other embodiments, a button 36 may be located on either shoulder or both shoulders. In another embodiment, a button 36 may be positioned on the strap 32 such that it is located on a chest of the user 30.

The POC system 20 is lightweight and portable for recreational use. For example, the POC system 20 may be used for skiing or biking at high altitudes, where a user may need supplemental oxygen to make breathing at the high altitude easier. The POC system 20 may be used for other sporting activities at high altitude and extreme sporting generally. In some examples, the POC system 20 may be used on the sidelines during sporting events for exhausted players to recover more quickly.

It should be understood that the POC 22 includes a control unit programmed with executable instructions for interfacing with and operating the various components of the POC 22. For example, the control unit is programmed to maintain a boost function for a period of time upon activation of the button 36. The control unit is also responsive to the power button 29, and is operable to send information for display via display 33. The control unit is further programmed to provide the other functionality discussed above, among other features. It should be understood that the control unit could be part of an overall control module. The control unit includes hardware and software, and further includes a processing unit and non-transitory memory for executing the various control strategies and modes of the POC system.

It should be understood that terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A portable oxygen concentrator system, comprising:
   a case containing a portable oxygen concentrator having a filter configured to draw in ambient air, remove other gases, and deliver concentrated oxygen having an oxygen purity of less than 85% in normal conditions, wherein the portable oxygen concentrator is configured to operate at only a fixed base pulse flow and a boost pulse flow, wherein normal conditions includes the fixed base pulse flow and the boost pulse flow;
   a delivery system configured to deliver the concentrated oxygen from the portable oxygen concentrator to a user; and
   a button which, when activated, is configured to activate the boost pulse flow and cause the portable oxygen concentrator to deliver an increased flow of oxygen above the fixed base pulse flow to the user for a period of time.

2. The portable oxygen concentrator system of claim 1, comprising a pair of shoulder straps configured to secure the case to the user's back.

3. The portable oxygen concentrator system of claim 2, wherein the button is positioned on one of the shoulder straps.

4. The portable oxygen concentrator system of claim 1, wherein the base pulse flow is between 1 and 3 liters per minute.

5. The portable oxygen concentrator system of claim 1, wherein the user is an athlete.

6. The portable oxygen concentrator system of claim 1, wherein the fixed base pulse flow cannot be adjusted by a user.

7. The portable oxygen concentrator system of claim 1, wherein the base pulse flow is about 2 liters per minute, the boost pulse flow is about 5 liters per minute, and the period of time is about 5 minutes.

8. A portable oxygen concentrator, comprising:
   a case containing a portable oxygen concentrator including a filter configured to draw in ambient air, remove other gases, deliver concentrated oxygen having an oxygen purity of less than 85% in normal conditions; and
   wherein the portable oxygen concentrator is configured to deliver oxygen only at a fixed base pulse flow and a fixed boost pulse flow, wherein the fixed base pulse flow and the fixed boost pulse flow cannot be adjusted by a user, and wherein normal conditions includes the fixed base pulse flow and the boost pulse flow.

9. The portable oxygen concentrator of claim 8, wherein the filter is configured to deliver an oxygen purity of less than about 80%.

10. The portable oxygen concentrator of claim 8, wherein the portable oxygen concentrator has a power button and a boost button, the boost button being configured to activate the fixed boost pulse flow for a period of time.

11. The portable oxygen concentrator of claim 10, wherein the portable oxygen concentrator only has two buttons.

12. The portable oxygen concentrator of claim 10, wherein the period of time is between 2 and 10 minutes.

13. The portable oxygen concentrator of claim 8, wherein the portable oxygen concentrator has a shoulder strap and is configured to be worn on a user's back.

14. A portable oxygen concentrator system, comprising:
a case containing a portable oxygen concentrator, wherein the portable oxygen concentrator has a base pulse flow and a boost pulse flow, and can only be used at either the base pulse flow or the boost pulse flow, and wherein the base pulse flow is fixed between about 1 and about 3 liters per minute.

15. The portable oxygen concentrator system of claim 14, wherein the boost pulse flow is configured to be activated by the boost button and the boost pulse flow is fixed between about 2 and about 5 liters per minute and lasts for a period of time, after which the system returns to the base pulse flow.

16. The portable oxygen concentrator system of claim 15, wherein the period of time is between 1 and 10 minutes.

17. The portable oxygen concentrator system of claim 15, wherein the base pulse flow is about 2 liters per minute and the boost pulse flow is about 5 liters per minute.

18. The portable oxygen concentrator system of claim 15, wherein the period of time is about 5 minutes.

19. The portable oxygen concentrator system of claim 14, wherein the boost pulse flow is configured to be activated by a button on a shoulder strap of the case.

20. The portable oxygen concentrator system of claim 14, wherein the case has a pair of shoulder straps and is configured to be worn on a user's back.

* * * * *